United States Patent [19]
Jensen et al.

[11] Patent Number: 5,704,905
[45] Date of Patent: Jan. 6, 1998

[54] WOUND DRESSING HAVING FILM-BACKED HYDROCOLLOID-CONTAINING ADHESIVE LAYER WITH LINEAR DEPRESSIONS

[76] Inventors: Ole R. Jensen; Jarl B. Jensen, both of 646 Orangeburgh Rd., River Vale, N.J. 07675

[21] Appl. No.: 543,869

[22] Filed: Oct. 10, 1995

[51] Int. Cl.⁶ ............... A61F 13/00; A61F 13/02
[52] U.S. Cl. .................. 602/58; 602/42; 602/43
[58] Field of Search ............... 602/41–43, 54, 602/55, 58, 57; 128/846, 888, 889, 284; 604/386, 389, 358, 304

[56] References Cited

U.S. PATENT DOCUMENTS

| | | | |
|---|---|---|---|
| 1,845,630 | 2/1932 | Scholl | 602/58 |
| 2,706,476 | 4/1955 | Diamond | 128/889 |
| 3,339,546 | 9/1967 | Chen . | |
| 3,625,209 | 12/1971 | Clark . | |
| 3,670,731 | 6/1972 | Harmon | 602/42 |
| 4,192,312 | 3/1980 | Wilson . | |
| 4,214,582 | 7/1980 | Patel . | |
| 4,231,369 | 11/1980 | Sorensen et al. . | |
| 4,360,015 | 11/1982 | Mayer | 602/42 X |
| 4,360,021 | 11/1982 | Stima | 602/42 |
| 4,477,325 | 10/1984 | Osburn . | |
| 4,612,230 | 9/1986 | Liland et al. . | |
| 4,674,510 | 6/1987 | Sneider . | |
| 4,699,134 | 10/1987 | Samuelsen . | |
| 4,738,257 | 4/1988 | Meyer et al. . | |
| 4,798,200 | 1/1989 | Warthen et al. . | |
| 4,867,146 | 9/1989 | Krupnick et al. . | |
| 4,867,748 | 9/1989 | Samuelsen . | |
| 4,965,126 | 10/1990 | Abraham et al. . | |
| 5,000,172 | 3/1991 | Ward . | |
| 5,012,801 | 5/1991 | Feret . | |
| 5,092,323 | 3/1992 | Riedel et al. | 128/888 X |
| 5,106,629 | 4/1992 | Cartmell et al. . | |
| 5,115,801 | 5/1992 | Cartmell et al. . | |
| 5,133,821 | 7/1992 | Jensen . | |
| 5,176,703 | 1/1993 | Peterson . | |
| 5,250,043 | 10/1993 | Castellana et al. . | |
| 5,263,970 | 11/1993 | Preller . | |
| 5,265,605 | 11/1993 | Afflerbach . | |
| 5,356,372 | 10/1994 | Donovan et al. . | |
| 5,386,835 | 2/1995 | Elphick et al. | 128/846 |
| 5,429,592 | 7/1995 | Jensen . | |
| 5,486,158 | 1/1996 | Samuelson | 602/43 |

FOREIGN PATENT DOCUMENTS

| | | |
|---|---|---|
| 0 621 042 A1 | 10/1994 | European Pat. Off. . |
| 0 341 045 | 11/1994 | European Pat. Off. . |
| G 94 15 058.3 | 11/1994 | Germany . |
| 2 148 125 A | 5/1985 | United Kingdom . |
| 2 191 403 A | 12/1987 | United Kingdom . |
| WO 92/05755 | 4/1992 | WIPO . |
| WO 93/00056 | 1/1993 | WIPO . |
| WO 93/08777 | 5/1993 | WIPO . |
| WO 95/14451 | 6/1995 | WIPO . |

*Primary Examiner*—Richard J. Apley
*Assistant Examiner*—Denise Pothier
*Attorney, Agent, or Firm*—Brinks Hofer Gilson & Lione

[57] ABSTRACT

A wound dressing is disclosed in which a thin layer of a hydrocolloid-containing adhesive material is covered on one side by a flexible, transparent or semi-transparent backing film and, on the other side, by one or more removable release sheets. Linear depressions are provided along the film-backed side of the adhesive layer and are clearly visible through the backing film to serve as guide lines, flex lines, and/or hinge lines in the use of the dressing. A foldable sacral dressing embodying such features is specifically disclosed.

41 Claims, 3 Drawing Sheets

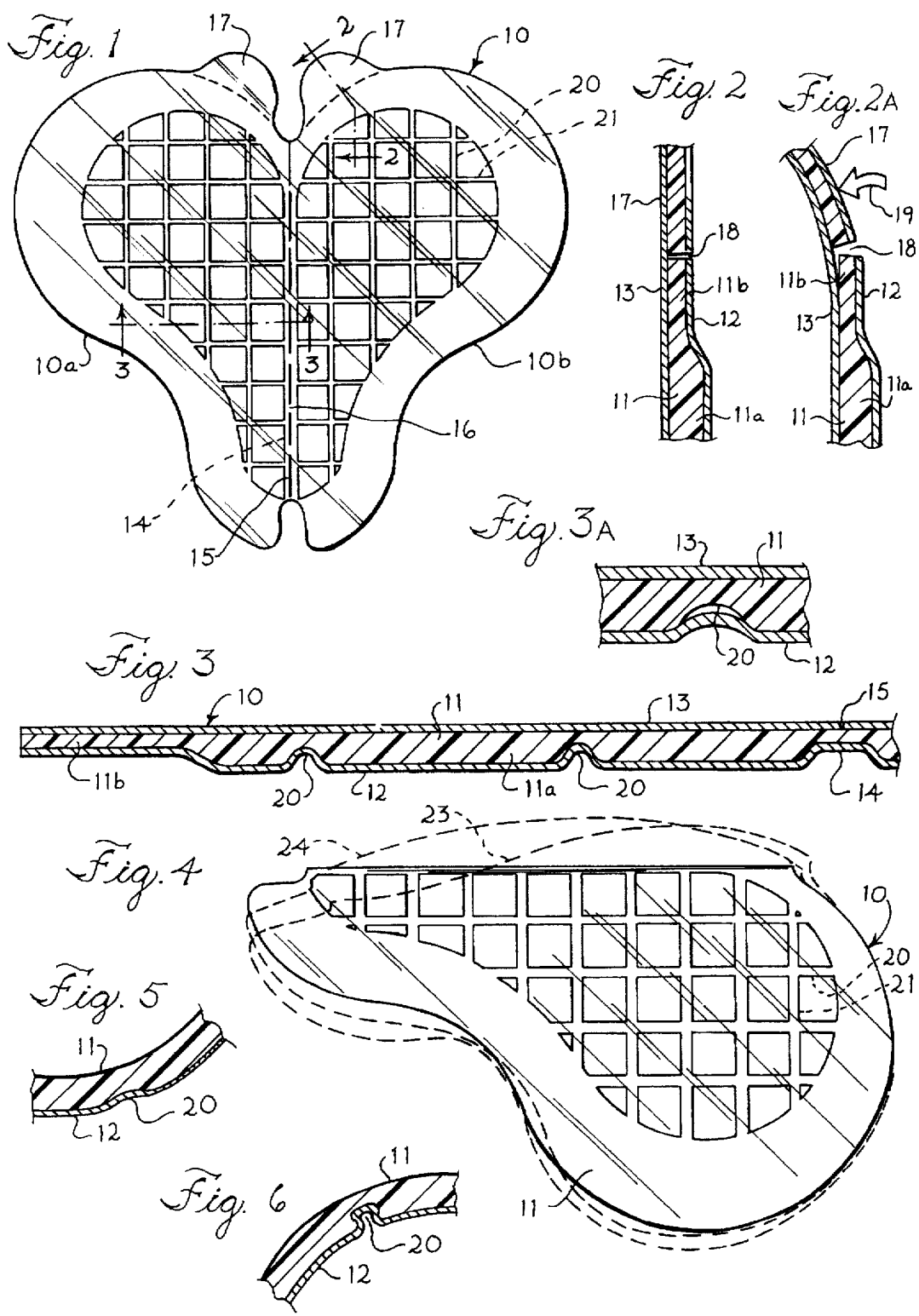

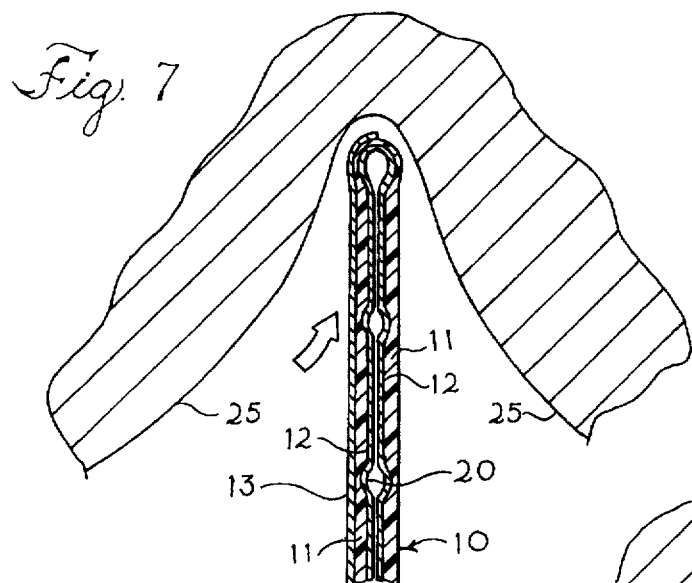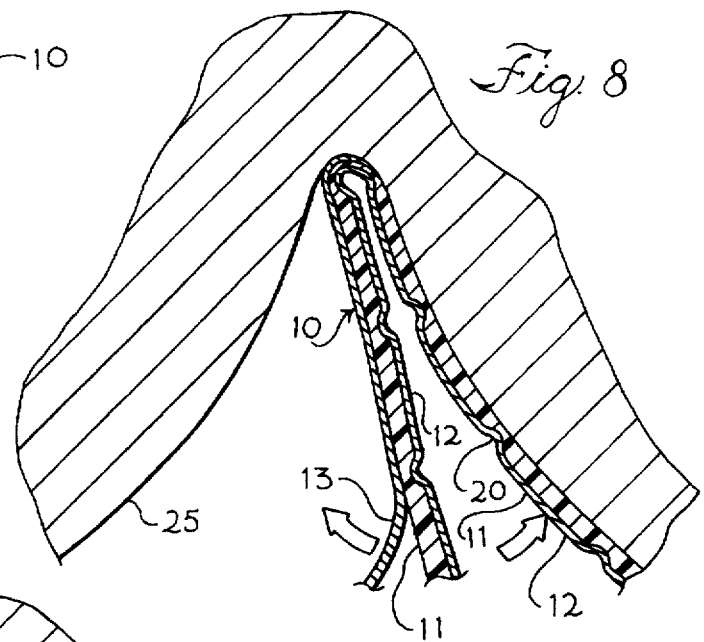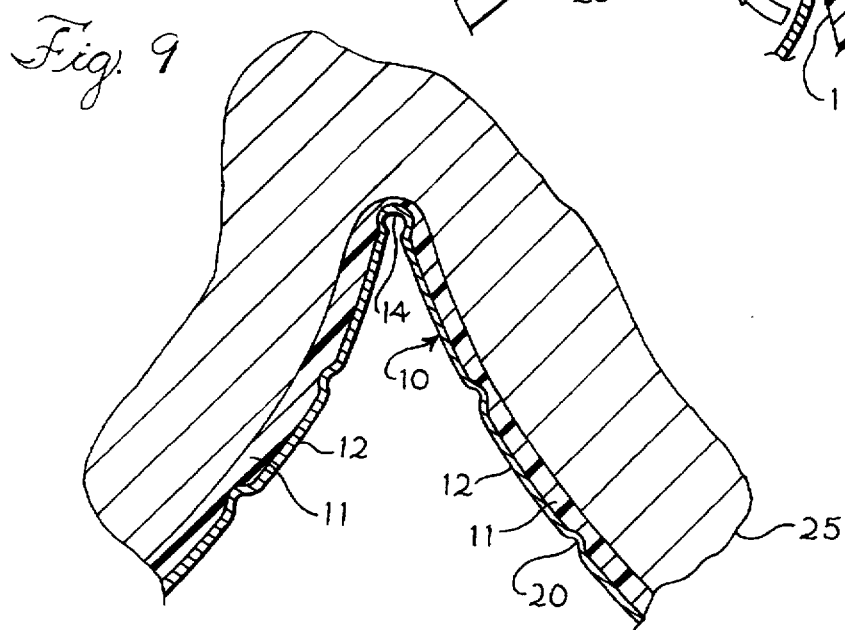

WOUND DRESSING HAVING FILM-BACKED HYDROCOLLOID-CONTAINING ADHESIVE LAYER WITH LINEAR DEPRESSIONS

BACKGROUND AND SUMMARY

For years it has been a common practice to provide users of wound dressings with transparent sheets on which grid patterns are imprinted. The grid pattern may be imprinted directly on the transparent backing film of such a dressing, or upon the dressing's transparent release sheet (which is peeled away at the time of application), or upon a separate transparent sheet supplied to the user along with the dressing. In any case, the imprinted grid pattern is helpful in wound assessment and is particularly useful in recording the size, and changes in size, of wounds such as decubitus ulcers and pressure sores. For example, a transparent sheet imprinted with such a grid pattern may be placed over a wound site and the shape and size of the wound may be traced onto the transparent sheet to serve as a record of the condition of the wound at a given date. References relevant to such usage are U.S. Pat. Nos. 4,965,126, 5,106,629, 5,000,172, and 5,265,605.

A multilayer wound dressing commonly used for decubitus ulcers and pressure sores takes the form of a pliant, fluid-absorbing, hydrocolloid-containing adhesive layer having both wet and dry tack and backed by a transparent or translucent elastomeric film. A typical adhesive material used for such a dressing may be composed of a tacky elastomer such as polyisobutylene in which hydrocolloid particles are uniformly dispersed. The preferred hydrocolloids may include any water-soluble gum such as pectin, gelatin, carboxymethylcellulose, sodium/calcium alginate fibers, polysaccharides and the like. The wound contacting surface of the hydrocolloid-containing adhesive material is maintained in sterile, protected condition until the time of application by one or more removable release sheets. Reference may be had to U.S. Pat. Nos. 4,738,257, 4,477,325, 4,231,369, 5,429,592 and 3,339,546 for details of wound dressings embodying such features, and to U.S. Pat. No. 5,133,821 for a continuous method for making hydrocolloid wound dressings of contoured shapes.

While it is advantageous to the user to have a dressing imprinted with grid markings on its backing film or release sheet, or to be provided with a separate transparent sheet that is so imprinted, the imprinting operation adds at least one further step in the manufacture of the product and necessarily incurs additional costs. Also, precautions must be taken, especially where the imprinted grid is part of the dressing itself, to avoid the use of inks that might act as irritants or cause other undesirable effects. Even where an ink is known to be non-toxic and hypoallergenic, it is nevertheless a colorant and care must be taken to avoid the risk that such a colorant does not bleed or transfer into the wound as the hydrocolloid dressing becomes hydrated in use.

Accordingly, it is an important aspect of this invention to provide a wound dressing that has one or more linear depressions that assist a user in applying, flexing or folding of the dressing, and are preferably arranged as guide lines for orienting the dressing and measuring the size and shape of a wound, without the disadvantages associated with prior dressings having imprinted ink markings. A dressing embodying this invention may have an arrangement of lines, such as a grid arrangement, that is achieved without the use of inks and without any additional production steps or significant additional production costs.

Briefly a wound dressing constituting a preferred embodiment of this invention includes a pliant, translucent, hydrocolloid-containing adhesive layer and a flexible transparent or semi-transparent backing film secured to one side of that adhesive layer. A release sheet, ideally in separable sections, is removably secured to the opposite side of the adhesive layer. Most advantageously, the release sheet is transparent, so that the dressing as a whole has a sufficient degree of transparency to allow the outline of a wound to be viewed through all layers of the dressing.

One side of the adhesive layer (the side directly beneath the backing film) has at least one linear depression that is visible through the film. The depression can be distinguished visually because the thickness of the adhesive layer in that depression is substantially less than the thickness of the adhesive layer alongside the depression. Visibility may also be enhanced if the backing film fails to match the contour of the adhesive layer within the depression and instead bridges, or at least partially bridges, that depression. Where such bridging occurs, the refractive and reflective effects are such that the linear depression appears as a light-colored line and is readily distinguishable from adjacent portions of the dressing where the backing film (preferably semi-transparent) makes direct surface contact with the translucent hydrocolloid layer.

The linear depression, especially if straight, may serve as a hinge line for facilitating folding of the dressing. Such a construction is particularly advantageous where the dressing is intended to be applied to ulcers or pressure sores in the sacral region. In such a case, the straight linear depression in the adhesive layer defines a line of symmetry between two sections of the dressing, and the release sheet may be provided with a slit (or a longitudinal series of slits) extending along the hinge line so that the release sheet sections may be sequentially removed to facilitate application of the dressing.

The adhesive layer may additionally, or alternatively, be provided with a multiplicity of such linear depressions defining a pattern of fold lines that may also serve as guide lines visible through the transparent or semi-transparent backing film. The linear depressions of the pattern may be straight or curved. If they are curvilinear, they may be concentrically arranged to assist in visual placement of the dressing and to serve as measuring guides for assessing the size and shape of a wound.

Instead of being curvilinear, the linear depressions in the adhesive layer may be straight. One set of spaced parallel depressions may extend at right angles to a second set of spaced parallel depressions to form a measuring grid visible through the transparent or semi-transparent backing film of the dressing. In addition, such depressions, whether straight or curvilinear, may serve as fold lines that enhance the flexibility and anatomical conformability of the dressing. It has been found that depending on the direction of flexure, the linear depressions may increase or decrease in width, allowing such a dressing to assume multiple curvatures as well as changes in such curvatures that necessarily occur with patient movement.

In a preferred embodiment of the invention, the dressing, although generally planar, is contoured to the extent that it is provided with a peripheral border portion in which the hydrocolloid-containing adhesive material is of reduced thickness. Ideally, the thickness of the adhesive layer along that border is substantially the same as the thickness of the adhesive layer in the linear depression(s), or is at least no greater than in such depression(s), so that any such depression extending towards a border portion will terminate at that border portion rather than continue to the outer limits of the dressing and function as a channel for liquid migration and possible leakage when the hydrocolloid-containing adhesive layer becomes hydrated in use.

Other features, advantages, and objects of the invention will become apparent from the specification and drawings.

DRAWINGS

FIG. 1 is a plan view of a wound care dressing for sacral placement embodying the invention.

FIG. 2 is an enlarged sectional view taken along line 2—2 of FIG. 1.

FIG. 2A illustrates the structure of FIG. 2 when a tab portion is flexed to commence removal of the release sheet.

FIG. 3 is an enlarged sectional view taken along line 3—3 of FIG. 1.

FIG. 3A is a still further enlarged fragmentary sectional view showing a portion of a dressing similar to that depicted in FIG. 3 but with the polymeric backing film of the dressing bridging a depression in the hydrocolloid-containing adhesive layer.

FIG. 4 is a side view of the dressing after its release sheet has been removed and the dressing has been folded, with broken lines depicting different curvatures such dressing may readily assume for anatomical conformity.

FIGS. 5 and 6 are enlarged fragmentary sectional views illustrating the relationships of the adhesive layer and backing layer in the area of a linear depression depending on whether the curvature of the dressing is concave or convex.

FIGS. 7–9 are somewhat schematic sectional views depicting the steps of applying the sacral dressing depicted in FIGS. 1–6.

DETAILED DESCRIPTION OF PREFERRED EMBODIMENTS

Figure 10:
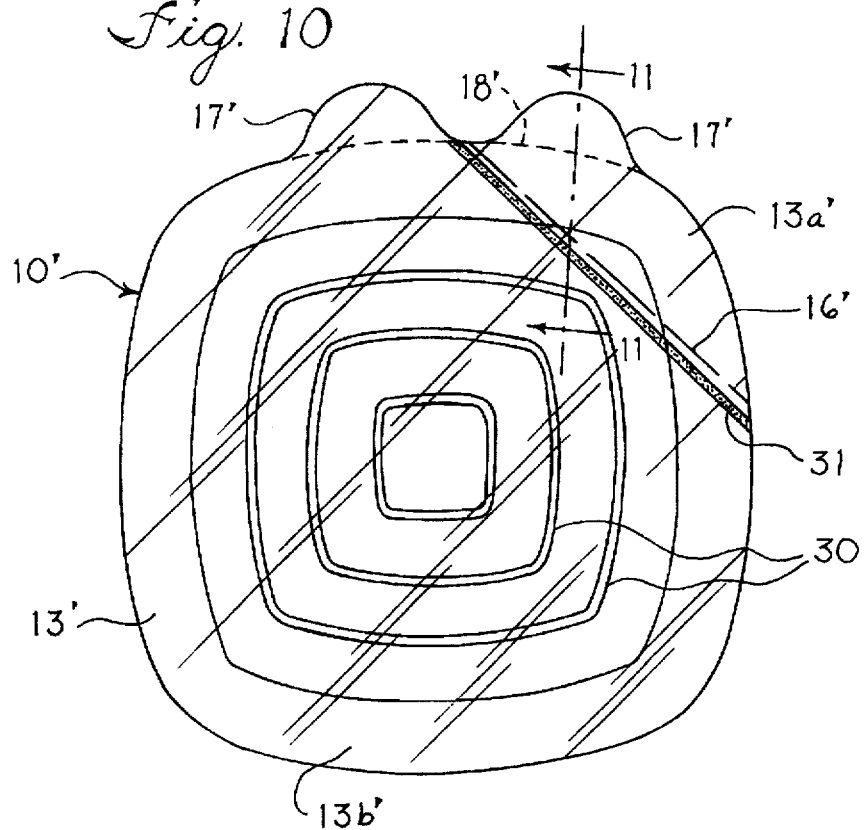
FIG. 10 is a plan view of a wound dressing constituting a second embodiment of the invention.

Referring to FIGS. 1–9 of the drawings, the numeral 10 generally designates a wound dressing suitable for use in the care and treatment of decubitus ulcers and pressure sores, although the general features of the dressing also make it suitable for use with other types of wounds. The particular dressing depicted in FIG. 1 is generally planar and pear-shaped (or heart-shaped) in outline. That shape, in combination with other features, including a central fold line at 15 that provides the symmetrical dressing with two half sections 10a and 10b of identical size and shape, makes the illustrated dressing especially suitable for sacral placement. It has been estimated that 50 percent or more of the pressure sores experienced by patients who are bedridden or confined to wheelchairs occur in the sacral region just below the coccix. It is to be understood, however, that while a sacral dressing is shown for purposes of illustration, dressings of other shapes, intended for application to other areas of the body, may also utilize the features of this invention.

Dressing 10 is comprised of three layers: an adhesive layer 11 that is soft, pliant, and composed essentially of a tacky adhesive material having one or more hydrocolloids dispersed therein, a backing film 12 along one side of the adhesive layer, and a removable release sheet (or sheets) 13 along the opposite side of the adhesive layer. The backing film 12 should be transparent or semi-transparent, highly flexible, stretchable, and (preferably) elastically recoverable. An elastomeric film formed of polyurethane has been found particularly effective, but films of other materials, such as low molecular weight polyethylene or polyvinyl chloride, may be used.

The removable release sheet 13 should also be flexible but, unlike the backing film 12, it is preferably non-stretchable and therefore incapable of assuming double curvatures. It functions to protect the planar bodyside surface of the adhesive layer against contamination prior to use and makes the dressing easier to handle and control during application. While the release sheet might be formed of an opaque material such as siliconized paper, it is particularly advantageous if such sheet is formed from a transparent polymeric material. One such material that has been found particularly effective is polyethylene terephthalate, but other transparent and dimensionally stable plastic materials having similar properties may be used.

It is particularly advantageous if the adhesive layer 11 is translucent at least to a limited extent. The term "translucent" is here used to mean that while the layer may appear milky or colored because of its hydrocolloid content, it is nevertheless sufficiently transparent for the shape and size of a wound to be viewed therethrough. Such an adhesive material is well-known and generally consists of a hydrocolloid, or a mixture of hydrocolloids, dispersed in a viscous, water-insoluble, elastomeric binder. The adhesive material may contain from about 50 to 70% by weight of a water soluble or swellable hydrocolloid, or a mixture of such hydrocolloids, such as sodium carboxymethylcellulose, calcium carboxymethylcellulose, pectin, gelatin, high molecular weight carbowax, carboxypolymethylene, polyvinyl alcohol, polyacrylates and other finely-divided moisture-absorbing and swellable materials, dispersed in about 50 to 50% by weight of a viscous elastomer such as polyisobutylene, natural rubber, silicone rubber, acrylonitrile rubber, or polyurethane rubber. As disclosed in U.S. Pat. No. 3,339,546, an effective adhesive composition is believed to be composed of polyisobutylene in which is dispersed a mixture of approximately equal percentages by weight of sodium carboxymethylcellulose, pectin and gelatin.

The translucency of the adhesive layer is dependent on its thickness as well as its composition. In general, it is believed that for adequate translucency, the thickness of the adhesive layer throughout the body of the dressing should not be more than about 3.0 mm and, preferably, should not exceed about 1.0 mm.

In the embodiment of the dressing depicted in the drawings, the dressing is contoured so that the adhesive layer 11 has a relatively thick body portion 11a and a peripheral border portion 11b of reduced thickness. The contouring is shown on the side of the adhesive layer covered by backing film 12, the opposite side of the adhesive layer (and the opposite side of the dressing as a whole) being relatively flat or planar. Reference may be had to U.S. Pat. No. 5,133,821 for a continuous method for making a contoured wound dressing having a continuous peripheral border in which the adhesive layer is of reduced thickness. To prevent channeling and possible leakage, and to avoid or reduce the possibility that external moisture might disrupt the adhesive seal between border portion 11b and the skin, it is desirable that the thickness of the border portion of adhesive material be less than about 0.5 mm, and preferably less than about 0.2 mm. In addition, the width of the border portion should be no less than 5 mm and should preferably be 10 mm or more.

A linear depression 14 is provided in the adhesive layer 11 along the midline of the symmetrical dressing, such linear depression being straight and located (along the side of the adhesive layer covered by backing film 12.) Depression 14 defines a hinge line to facilitate folding of the dressing as shown in FIGS. 4 and 7–9. Release sheet 13 is slitted at 15 along the length of depression 14 so that the release sheet may be removed in two sections, one such section extending over dressing section 10a and the other over dressing section 10b. While the line of separation of the two release sheet sections is shown in the form of a series of slits with rupturable connecting portions 16 joining the two sections together, it will be understood that, if desired, the slit in the release sheet may alternatively take the form of a single uninterrupted slit.

Removal of the sections of release sheet 13 is facilitated by tabs 17. As shown in FIGS. 2 and 2A, each tab 17 is an arcuate extension of the border portion of the dressing. Die cut lines 18 follow the general outline of the dressing (exclusive of the tabs), with such die cut lines extending only through the backing film 12 and the adhesive layer 11b. As illustrated in FIG. 2A, each section of the release sheet 13 may therefore be peeled away from the adhesive layer 11 simply by gripping the tab and urging it in the direction of arrow 19.

In addition to the linear depression 14, the body portion 11a of the adhesive layer is provided with two sets of spaced parallel depressions 20 and 21. The depressions 20 of one set are parallel with the depression 14 that forms the hinge line having a length least half a fold line, and the depressions 21 of the other set extend at right angles thereto, so that the two sets together form a grid that may be seen through the -transparent or semi-transparent backing film 12. The thickness of the adhesive layer at the base of each such depression 20, 21 should be at least as great as the thickness of the border portion 11b of the adhesive layer so that, as shown in the drawings, the depressions which form the grid do not extend into the border of the dressing but stop at the outer limits of body portion 11a.

The straight linear depressions 20, 21 defining the grid are useful in wound assessment, that is, in visually assessing the size and shape of a wound at the time of dressing application. The grid is visible through the backing layer 12, because, among other things, the reduced thickness of the adhesive material in the linear depressions gives the adhesive layer greater transparency along those lines of depression. It has also been found that such visibility may be enhanced if the backing film bridges the depressions as indicated in FIG. 3A rather than maintaining contact with the adhesive layer throughout such depressions as depicted in FIG. 3. Such enhancement is believed to be caused by differences in reflection and refraction in the linear areas of non-attachment, making the depressions 20 and 21 noticeably lighter and more milky in appearance than the adjacent areas where the backing film 12 is in direct surface contact with the adhesive layer 11. Such non-attachment may be achieved simply by applying the backing film 12 to the adhesive layer 11 in a final laminating step so that the film spans the depressions formed in the adhesive layer in an earlier contouring step (see U.S. Pat. No. 5,133,821 for a two-step process), or it may occur because of detachment resulting from any of a number of factors, such as the composition of the adhesive material and its aggressiveness, the width of the depressions, the composition and thickness of the backing film 12, and the conditions of operation of the process disclosed in the aforementioned patent. It has also been found that a backing film that is not only stretchable but elastically recoverable, such as a polyurethane film, tends to pull away from the adhesive material within such depressions as depicted in FIG. 3 even if the film is directed into such depressions during manufacture.

In addition to providing a visible grid for wound assessment, the linear depressions 20 and 21 also enhance the flexibility and conformability of the dressing. Thus, FIG. 5 illustrates that such a depression 20 becomes wider when the dressing is flexed so that the backing layer 12 assumes a convex curvature, and FIG. 6 illustrates that the depression becomes narrower when the dressing is flexed so that the backing layer 12 assumes a concave curvature.

Conformability is believed important in all wound dressings, but it is a particular advantage for a sacral dressing of the type depicted in FIGS. 1–9. FIG. 4 illustrates the dressing after it has been folded along the straight linear depression 14 and its release sheet 13 has been completely removed. The multiplicity of intersecting depressions 20 and 21 that define the grid, in combination with the pliability of the hydrocolloid-containing adhesive layer 11 and the flexibility and stretchability of backing layer 12, permit the dressing to assume various multiple curvatures as indicated by broken lines 23 and 24.

In use, the sacral dressing is first folded along its midline and one of the sections of release sheet 13 is removed (FIG. 7). The folded dressing is placed between the buttocks 25 and the section of the dressing with its uncovered adhesive layer is brought into adhesive sealing contact with the patient (FIG. 8). Thereafter, the other section of the release sheet 13 is removed, and the second section of the dressing is brought into adhesive contact with the patient (FIG. 9).

Figure 11:
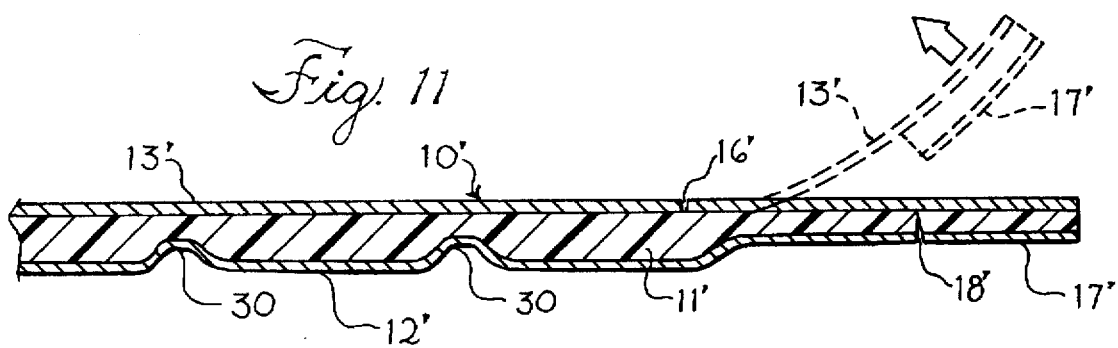
FIG. 11 is an enlarged sectional view taken along line 11—11 of FIG. 10.

FIGS. 10 and 11 illustrate a second embodiment of the invention. As in the first embodiment, dressing 10' consists essentially of an adhesive layer 11' covered on one side by a backing film 12' and on the other side by a release sheet 13'. The compositions of the three layers are the same as those described in connection with the first embodiment. The main differences lie in the different shape of dressing 10' and the arrangement of linear depressions in the surface of the adhesive layer 11' covered by backing film 12'.

Dressing 10' has the outline of a rounded square and its linear depressions 30 are curvilinear and concentric. Preferably, they are uniformly spaced apart as shown in FIG. 10. Release sheet 13' may be slit across one corner as indicated at 16', and a pair of ears or tabs 17', formed in the same manner as described in connection with the first embodiment, may be provided to facilitate removal of the two sections of the release sheet. If desired, a stripe 31 may be imprinted on the release sheet to serve as a visible locator for slit 16'. Reference may be had to U.S. Pat. No. 5,429,592 for further information concerning the use of such a stripe in conjunction with a slitted release sheet for a wound dressing.

As in the first embodiment, it is particularly desirable for the linear depressions 30 in the adhesive layer to be visible through the backing film so that they may assist a user in properly orienting the dressing over a wound and in assessing the size, shape and condition of the wound, at the time of application of the dressing. The depressions 30 also enhance flexure and anatomical conformity of the dressing in the same manner as described in connection with FIGS. 5 and 6. Again, it has been found that if the backing film bridges, or partially bridges, the linear depressions in the adhesive layer, such depressions become even more visible through the backing film.

As noted, slit 16' extends across one corner of the dressing, dividing release sheet 13 into two sections 13a' and 13b' of unequal size. Such an arrangement facilitates application of the dressing and also provides the transparent release sheet with an additional function in would assessment.

With regard to application, a user first removes the large release sheet section 13b' and applies the sterile surface of the uncovered adhesive layer 11' to the wound site, holding the dressing as it is so applied by that corner portion still covered by the smaller release sheet section 13a'. Application of the dressing to the patient is then completed by removing the smaller section 13a' by means of its tab 17'.

As to the additional function, the larger removed section 13b' of the release sheet may then be placed over the applied dressing and the user, viewing the wound through that dressing and the transparent release sheet, may trace the outline of the wound onto the section 13b' by means of a pen or other suitable marking instrument. Section 13b' may then be placed in a record file for future reference in assessing changes in the size, shape and condition of the wound.

While the dressing 10' is shown with curvilinear depressions 30, it will be understood that, if desired, such a dressing may instead be provided with straight intersecting lines of depression, forming a measuring grid as shown and described in connection with dressing 10. Conversely, dressing 10 may instead be provided with curvilinear depressions of the type shown in FIGS. 10 and 11 rather than the straight linear depressions 20 and 21 shown in FIG. 1.

While embodiments of the invention have been disclosed in considerable detail for purposes of illustration, it will be understood by those skilled in the art that many of these details may be varied without departing from the spirit and scope of the invention.

We claim:

1. A wound dressing comprising:
   a pliant, hydrocolloid containing adhesive layer;
   a flexible backing film secured to one side of said adhesive layer; and
   a release sheet removably secured to the opposite side of said adhesive layer; said one side of said adhesive layer covered by said backing film and having at least one linear depression visible through said backing film, the thickness of said adhesive layer in said depression being less than the thickness of said adhesive layer alongside said depression, said backing film spaced from said adhesive layer in said depression and bridging over at least a portion of said depression.

2. The wound dressing of claim 1 in which said adhesive layer is translucent.

3. The wound dressing of claim 1 wherein said at least one linear depression constitutes a hinge line for folding said dressing.

4. The wound dressing of claim 3 wherein said release sheet is slit along at least one slit line.

5. The wound dressing of claim 1 wherein said at least one linear depression further comprises a first set of linear depressions; said linear depressions of said first set being spaced uniformly apart in parallel relation to each other.

6. The wound dressing of claim 5 further comprising a second set of said straight linear depressions uniformly spaced apart and parallel to each other; said linear depressions of said second set being arranged at right angles to the depressions of said first step.

7. The wound dressing of claim 5 wherein one of said linear depressions defines a central fold line between first and second sections of said wound dressing.

8. The wound dressing of claims 1 further comprising a border portion extending along an outer edge of said dressing; the thickness of said adhesive layer along said border portion being the same as the thickness of said adhesive layer within said linear depression.

9. The wound dressing of claim 1 wherein said dressing is pear-shaped in outline.

10. The wound dressing of claim 1 wherein said dressing is substantially rectangular-shaped in outline.

11. The wound dressing of claim 1 wherein said dressing defines an outline that is at least partially curvilinear.

12. The wound dressing of claim 1 wherein the flexible backing film comprises a transparent material.

13. The wound dressing of claim 1 wherein the flexible backing film comprises a semi-transparent material.

14. A wound dressing comprising:
   a pliant, hydrocolloid containing adhesive layer comprising a first surface and a second surface, the first surface comprising a plurality of linear depressions, each depression defined by an area of reduced thickness of the adhesive layer relative to the thickness of the adhesive layer adjacent to the depressions, the linear depressions arranged in a grid pattern defined by a first set of said linear depressions spaced substantially in parallel relation to each other and a second set of said linear depressions substantially at a right angle to the first set of linear depressions;
   a flexible backing film secured to the first surface of the adhesive layer; and
   a release sheet removably secured to the second surface of the adhesive layer.

15. The wound dressing of claim 14 in which said adhesive layer is translucent.

16. The wound dressing of claim 14 further comprising a hinge linear depression in said adhesive layer, said hinge linear depression defined by an area of reduced thickness of the adhesive layer relative to the thickness of the adhesive layer adjacent to the hinge linear depression, said hinge linear depression located along a hinge line for folding said dressing.

17. The wound dressing of claim 14 further comprising a border portion extending along an outer edge of said dressing; the thickness of said adhesive layer along said border portion being the same as the thickness of said adhesive layer within said linear depression.

18. The wound dressing of claim 14 wherein said release sheet is slit along at least one slit line.

19. The wound dressing of claim 14 wherein said dressing is pear-shaped in outline.

20. The wound dressing of claim 14 wherein said dressing is substantially rectangular-shaped in outline.

21. The wound dressing of claim 14 wherein said dressing defines an outline that is at least partially curvilinear.

22. The wound dressing of claim 14 wherein said backing film bridges over at least a portion of said depression, said backing film spaced from said adhesive layer in said depression.

23. The wound dressing of claim 14 wherein the flexible backing film comprises a transparent material.

24. The wound dressing of claim 14 wherein the flexible backing film comprises a semi-transparent material.

25. A wound dressing comprising:
   a pliant, hydrocolloid containing adhesive layer comprising a first surface and a second surface, the first surface comprising a hinge defined by an area of reduced thickness of the adhesive layer relative to the thickness of the adhesive layer adjacent to the hinge, the hinge extending linearly and having a length at least half of a fold line extending from one edge to an opposite edge of said dressing;

a flexible backing film secured to the first surface of the adhesive layer; and a release sheet removably secured to the second surface of the adhesive layer, wherein the hinge extends substantially to at least one edge of said dressing.

26. The wound dressing of claim 25 wherein said hinge extends linearly from a first edge of said dressing to a second edge of said dressing.

27. The wound dressing of claim 25 in which said adhesive layer is translucent.

28. The wound dressing of claim 25 further comprising a border portion extending along an outer edge of said dressing, the thickness of said adhesive layer along said border portion being the same as the thickness of said adhesive layer within said hinge.

29. The wound dressing of claim 25 wherein said release sheet is slit along at least one slit line.

30. The wound dressing of claim 25 wherein said dressing is pear-shaped in outline.

31. The wound dressing of claim 25 wherein said dressing is substantially rectangular-shaped in outline.

32. The wound dressing of claim 25 wherein said dressing defines an outline that is at least partially curvilinear.

33. The wound dressing of claim 25 wherein the flexible backing film comprises a transparent material.

34. The wound dressing of claim 25 wherein the flexible backing film comprises a semi-transparent material.

35. A wound dressing comprising:

a pliant, hydrocolloid containing adhesive layer comprising a first surface and a second surface, the first surface comprising a plurality of linear depressions, each depression defined by an area of reduced thickness of the adhesive layer relative to the thickness of the adhesive layer adjacent to the depressions, one of said plurality of depressions defining a hinge line for folding the dressing, the remaining linear depressions arranged in a grid pattern defined by a first set of said linear depressions spaced substantially in parallel relation to each other and a second set of said linear depressions substantially perpendicular to the first set of linear depressions;

a flexible backing film secured to the first surface of the adhesive layer, said backing film spaced from said adhesive layer in said depression bridging over at least a portion of said depression; and a release sheet removably secured to the second surface of the adhesive layer, said release sheet including a slit along said hinge line.

36. The wound dressing of claim 35 further comprising a border portion extending along an outer edge of said dressing; the thickness of said adhesive layer along said border portion being the same as the thickness of said adhesive layer within said linear depression.

37. The wound dressing of claim 35 wherein said dressing is pear-shaped in outline.

38. The wound dressing of claim 35 wherein said dressing is substantially rectangular-shaped in outline.

39. The wound dressing of claim 35 wherein said dressing defines an outline that is at least partially curvilinear.

40. The wound dressing of claim 35 wherein the flexible backing film comprises a transparent material.

41. The wound dressing of claim 35 wherein the flexible backing film comprises a semi-transparent material.

* * * * *